United States Patent [19]

Malbec

[11] 4,177,808
[45] Dec. 11, 1979

[54] ANTI-BUBBLE SAFETY VALVE FOR A LIQUID-CIRCUIT

[76] Inventor: Edouard Malbec, Logis de Chalonne, Le Gond Pontouvre, France, 16160

[21] Appl. No.: 834,545

[22] Filed: Sep. 19, 1977

[51] Int. Cl.$^2$ .................................. A61M 05/00
[52] U.S. Cl. .......................... 128/214 R; 128/274; 137/171; 137/403; 137/510
[58] Field of Search ........... 128/214 R, 214 C, 214 D, 128/214.2, 274; 137/171, 197, 403, 510

[56] References Cited

U.S. PATENT DOCUMENTS

| | | | |
|---|---|---|---|
| 3,204,632 | 9/1965 | Hofstra et al. | 128/214 E |
| 3,204,633 | 9/1965 | Hofstra | 128/214 E |
| 3,216,419 | 11/1965 | Scislowicz | 128/214 C |
| 3,664,814 | 5/1972 | Koremura | 128/214 D |
| 3,833,013 | 9/1974 | Leonard | 137/171 |
| 3,993,062 | 11/1976 | Jess | 128/214 R |

FOREIGN PATENT DOCUMENTS 275500  8/1927  United Kingdom ................ 137/403

*Primary Examiner*—Dalton L. Truluck
*Attorney, Agent, or Firm*—Fleit & Jacobson

[57] ABSTRACT

The anti-bubble safety valve comprises a liquid-admission chamber which is partly delimited by a diaphragm in cooperating relation with a seating provided with an outlet pipe. Thus the liquid which is present within the chamber is directed into the diaphragm-seating interface and passed in laminar flow towards the outlet pipe. The chamber is provided with a passageway to the surrounding atmosphere for the discharge of any air bubble which may have been admitted.

3 Claims, 4 Drawing Figures

ANTI-BUBBLE SAFETY VALVE FOR A LIQUID-CIRCUIT

This invention relates to an anti-bubble safety valve for a liquid-circuit, in particular for a low-pressure circuit of the type employed in medical applications and especially in perfusion.

In order to obtain a uniform flow of liquid, it is recommended practice to have recourse to a metering pump but it is absolutely necessary in this case to prevent the formation of air bubbles in the injected liquid.

The present invention makes it possible to achieve this result in a simple and reliable manner by providing a valve which can in particular be produced at low cost and can thus be incorporated in single-purpose perfusion lines which are intended to be delivered in a sterile package.

The anti-bubble safety valve in accordance with the invention essentially comprises a chamber for the admission of liquid which is partly delimited by a diaphragm in cooperating relation with a seating provided with an outlet pipe so that the liquid which is present within the chamber is directed into the diaphragm-seating interface and passed in laminar flow towards said outlet pipe, said chamber being provided with a passageway to the surrounding atmosphere for the discharge of any air bubble which may have been admitted.

It will be noted in addition that a valve of this type advantageously has an intrinsic anti-return action. At the same time, a predetermined limitation of any increase in the selected operating pressure can also be obtained in a safe and reliable manner by means of the passageway to the surrounding atmosphere.

In a form of construction which is particularly advantageous from the point of view of production and capital cost, the diaphragm is taken from the wall of a flexible bag which forms said chamber, the seating being constituted by a small plate to which the diaphragm is bonded.

Further distinctive features will become apparent from the following description of two embodiments of the invention which are given by way of example, reference being made to the accompanying drawings in which.

Figure 1:
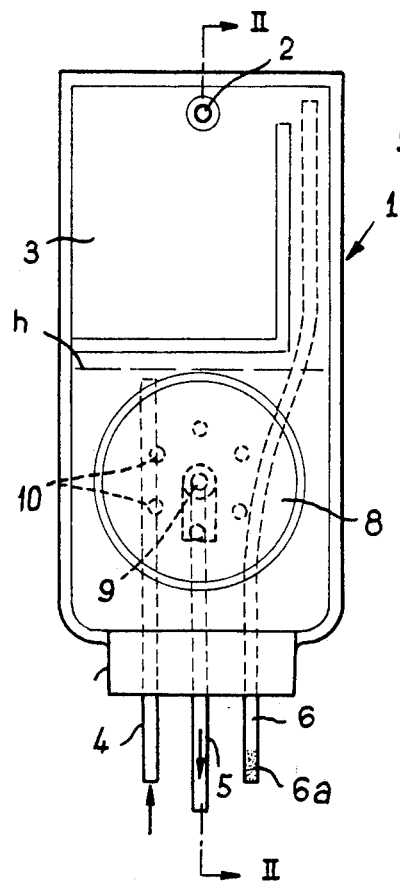
FIG. 1 is a front view in elevation of said valve.
Figure 2:
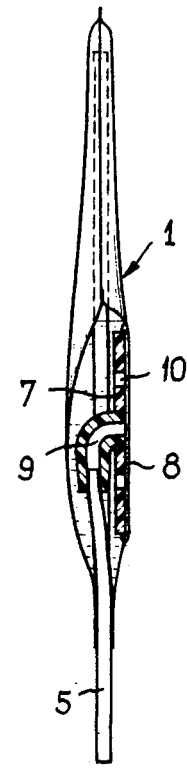
FIG. 2 is a partial sectional view of said valve taken along line II—II of FIG. 1.

The valve shown in FIGS. 1 and 2 is designed in the form of a flexible bag 1 of plastic material constituted in this case by two sheets which have been heat-sealed around their periphery in such a manner as to form in addition a hook-attachment eyelet 2 at the top portion of the bag as well as an upper pocket 3, the function of which will be explained hereinafter.

The bottom edge of the bag is bonded to three pipes: one pipe 4 serves to admit the liquid into the bottom of the bag, the liquid being supplied, for example, by means of a metering pump (not shown); a second pipe 5 constitutes a valve outlet pipe which is intended to be connected to a perfusion needle, for example; a third pipe 6 forms a vent and extends to the top portion of the bag above the inlet level of the pocket 3. The outlet of said vent 6 will normally be fitted with a cotton-wool plug 6a of the prescribed type.

The valve proper is constructed by means of a small plate 7 and a diaphragm 8 which is taken from a wall of the bag 1 and which, in this example, is bonded to the edge of the small plate by heat-sealing.

The small plate 7 thus forms a seating for the diaphragm and is provided with a central duct 9 to which the outlet pipe 5 of the valve is connected. Around said central duct 9, the small plate is provided with a series of holes 10 disposed in spaced relation around the duct 9 so that the liquid which is present within the bag is intended to pass through said holes, to spread over the interface between the diaphragm 8 and the small plate 7 and to pass towards the central duct 9 in laminar flow.

The mode of operation hereinabove described takes place in practice as follows.

When the liquid initially admitted into the bag via the pipe 4 reaches the level of the lower holes 10 of the small plate, said liquid has a tendency to spread by capillarity over the diaphragm 8/small plate 7 interface, thus "sticking" these latter to each other.

When the liquid reaches a predetermined height indicated for example by the line h in FIG. 1, it then thrusts the diaphragm 8 away from the small plate 7 and begins to flow in the laminar state until a level equilibrium is established within the bag. This equilibrium is dependent on the delivery of the feed pump which is accordingly placed within the outlet pipe 5.

If one or more air bubbles should happen to be introduced into the bag via the inlet pipe 4, said bubbles are normally carried away to the surface of the liquid which communicates with the surrounding atmosphere through the vent 6 and cannot in any event pass across the laminar-flow interface formed between diaphragm 8 and small plate 7.

Should an obstruction occur for any reason at the level of the perfusion (for example when the needle has come out of a vein), the level of liquid within the bag will rise until it overflows into the pocket 3 which will take a certain time to fill, thus enabling the nursing staff to notice the defect.

In the event of filling of the bag above the top level of the pocket 3, the liquid can still flow out through the vent 6 and no excessive overpressure can consequently be applied within the valve outlet pipe.

A diaphragm valve of this type also has an intrinsic anti-return action since the least reduction in pressure upstream of the holes 10 formed in the small plate tends to initiate closure of these latter by the diaphragm 8, with the result that any pulsations of the pump do not produce an effect of return of the liquid which is delivered.

Figure 4:
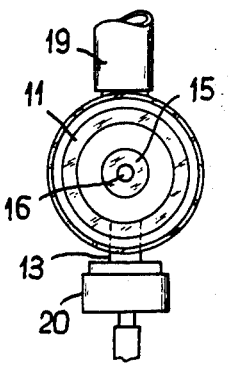
FIG. 4 is a view of said valve taken in the direction of the arrow IV of FIG. 3, the valve cover and diaphragm having been removed.
Figure 3:
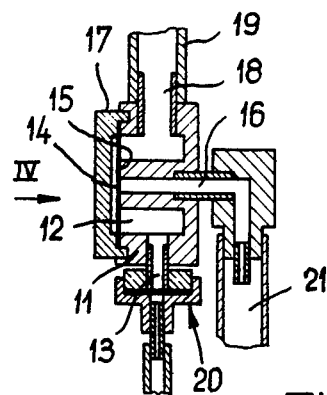
FIG. 3 is an axial sectional view of another embodiment of the valve.

In another form of construction of the valve in accordance with the invention as shown in FIGS. 3 and 4, the valve comprises a body 11 which forms an annular admission chamber 12 provided with an inlet duct 13. Said chamber is partly delimited laterally by a diaphragm 14 in cooperating relation with a seating 15 which is located within the annular chamber and transversed by an outlet duct 16. In this example, the diaphragm 14 is gripped at the periphery of the annular chamber by an end-cap 17 which is assembled with the body 11. A vent nozzle 18 is provided at the top of the chamber 12, the cross-sectional area of said nozzle being such that any bubble which may be introduced through the inlet duct 13 of smaller cross-sectional area may be readily permitted to escape. Said nozzle 18 is surmounted by a transparent tube 19 which permits observation of the height of liquid above the valve during operation and also serves as an overflow in the event that the pressure becomes excessive. Said tube can also be fitted with a cotton-wool plug of the prescribed type.

A further possibility of adding a filter capsule 20 at the valve inlet has also been illustrated in conjunction with this embodiment. Real microfiltering of the perfusion liquid can accordingly be obtained under the pressure of a feed pump and is superior to that which it is possible to obtain in a simple gravity-feed installation.

Another possibility which has also been illustrated consists in adding to the valve outlet pipe a drip-feed tube 21 which permits visual inspection of the liquid flow rate.

It is readily apparent that other alternative forms of construction can be devised without thereby departingeither from the scope or the spirit of the invention.

I claim:

1. An anti-bubble safety device for a low pressure liquid circuit and especially for medical perfusion, comprising a bag including a flexible wall and forming a chamber for the admission of liquid; a valve comprising a diaphragm forming a part of said flexible wall; a seating for said diaphragm formed by a plate having a peripheral edge to which is bonded said diaphragm, said diaphragm and seating forming an interface and comprising at least one liquid circulation passageway through the plate from the interior of the bag to the interface; and an outlet duct extending through said plate which is in laterally spaced relation with said at least one liquid circulation passageway so as to impose a laminar flow of the liquid in the interface between said passageway and said outlet duct, said outlet duct being adapted to be connected to an outlet pipe extending outwardly of the bag and said bag being provided with a passageway to the surrounding atmosphere.

2. A safety device as claimed in claim 1, wherein the bag includes suspension means for suspending the device, and wherein the device further comprises three pipes associated with the base of the bag, one pipe being provided for admission of the liquid into the bag, a second pipe being connected to the outlet duct, and a third pipe extending to the top portion of said bag and forming part of said passageway to the surrounding atmosphere.

3. A safety device as claimed in claim 3, wherein the bag is a flexible bag and has a pocket formed by bonding the bag walls to a level below that of the top of the third pipe so that said bag constitutes a liquid overflow volume in the event of overpressure which prevents normal discharge of the liquid through the device.

* * * * *